(12) United States Patent
Lin

(10) Patent No.: US 6,261,234 B1
(45) Date of Patent: Jul. 17, 2001

(54) METHOD AND APPARATUS FOR ULTRASOUND IMAGING WITH BIPLANE INSTRUMENT GUIDANCE

(75) Inventor: Gregory Sharat Lin, Fremont, CA (US)

(73) Assignee: Diasonics Ultrasound, Inc., Santa Clara, CA (US)

( * ) Notice: Subject to any disclaimer, the term of this patent is extended or adjusted under 35 U.S.C. 154(b) by 0 days.

(21) Appl. No.: 09/074,571

(22) Filed: May 7, 1998

(51) Int. Cl.[7] .................................................... A61B 8/14
(52) U.S. Cl. ................................ 600/461; 600/463
(58) Field of Search ......................... 600/437, 459, 600/439, 463, 472, 466, 467; 607/122; 128/916; 606/13, 14

(56) References Cited

U.S. PATENT DOCUMENTS

| | | | |
|---|---|---|---|
| 4,817,616 | | 4/1989 | Goldstein ................. 128/662.06 |
| 4,870,867 | * | 10/1989 | Shaulov .............................. 73/625 |
| 4,991,565 | | 2/1991 | Takahashi et al. ................. 128/4 |
| 5,433,198 | * | 7/1995 | Desai ............................ 607/122 |
| 5,474,071 | * | 12/1995 | Chapelon et al. ............. 600/439 |
| 5,577,502 | * | 11/1996 | Darrow et al. ................. 600/407 |
| 5,704,361 | | 1/1998 | Seward et al. ............... 128/662.06 |
| 5,713,363 | * | 2/1998 | Seward et al. ................. 600/437 |
| 5,776,067 | * | 7/1998 | Kamada et al. ................ 600/443 |
| 5,873,828 | * | 2/1999 | Fujio et al. .................... 600/439 |
| 5,876,345 | * | 3/1999 | Eaton et al. .................... 600/466 |
| 6,045,508 | * | 4/2000 | Hossack et al. ............... 600/463 |
| 6,066,096 | * | 5/2000 | Smith et al. ................... 600/463 |

FOREIGN PATENT DOCUMENTS

0139574A2   2/1985  (EP) .
WO94/13208  6/1994  (WO) .

* cited by examiner

*Primary Examiner*—Marvin M. Lateef
*Assistant Examiner*—Ali M. Imam
(74) *Attorney, Agent, or Firm*—Blakely, Sokoloff, Taylor & Zafman LLP

(57) ABSTRACT

Methods and apparatuses for providing simultaneous viewing of an instrument in two ultrasound imaging planes. An ultrasound imaging probe is provided which can generate at least two ultrasound imaging planes. In one embodiment, the two imaging planes are not parallel (i.e., the planes intersect). An instrument path is positioned with respect to the planes such that an instrument may be simultaneously viewed in both imaging planes. In one embodiment, the instrument path is provided at an intersection that, at least partially, defines the intersection of the two imaging planes.

36 Claims, 9 Drawing Sheets

METHOD AND APPARATUS FOR ULTRASOUND IMAGING WITH BIPLANE INSTRUMENT GUIDANCE

BACKGROUND OF THE INVENTION

1. Field of the Invention

The invention relates to the field of medical devices. More particularly, the invention relates to ultrasound endocavitary imaging devices.

2. Background Information

Various ultrasound techniques and devices have been developed for imaging the interior of a body (hereinafter, "body" refers to various types of subjects, such as humans, animals, non-living structures, etc.). One application of ultrasound imaging has been in the medical field, and in particular, in endocavitary probes (e.g., biopsy guidance endocavitary probes). Such probes may be used, for example, for endovaginal examination (e.g., to examine the uterus, ovaries, etc.), endorectal examination (e.g., to examine the rectal wall, prostate, etc.), and/or other medically-related applications. Typically, endocavitary probes include a linear array transducer positioned at the distal end of the probe that is to be inserted into a cavity of a body. The transducer provides an imaging plane for viewing structures/features of the body and/or another instrument (e.g., a biopsy needle) that, for example, may be guided into the body via the probe. The imaging plane may be provided at a side of a probe (corresponding to a "side-fire" transducer) or the front of the probe (corresponding to an "end-fire" transducer).

Since such linear array transducer endocavitary probes provide one imaging plane at any time for viewing the interior of the body and/or another instrument (e.g., a biopsy needle) that may be guided into the body via the probe, the ultrasound images provided by such probes are generally limited to a single plane. Unfortunately, such 2D (two-dimensional) images typically do not provide desired accuracy of structures/features within a body. In applications where a relatively high level of imaging accuracy may be critical, such as biopsy needle guidance through or in proximity to sensitive bodily structures which may need to be avoided by the needle, such linear array transducer probes may not be practical.

Several techniques for improving the above-mentioned limitation(s) of single linear array transducer endocavitary probes have been proposed, but each is relatively limited as well. For example, some endocavitary probes utilize a mechanical, rather than a linear array, transducer. Such mechanical transducer probes provide a single imaging plane at any one time, but the mechanical transducer may be rotated up to 180 degrees or even more to provide multiplane three-dimensional (3D) orientation in a field of view. However, end-fire multiplane single mechanical transducer probes cannot be used for biopsy guidance, since the biopsy needle is only visible in at most one plane of the rotation. Moreover, side-fire multiplane single mechanical transducer probes are unable to provide viewing of a forward-penetrating biopsy need at all.

In addition to the single-plane linear array transducer probes and the multiplane mechanical transducer probes described above, some biplane probes have been proposed. One type of a biplane probe utilizes a dual convex oblique end-fire linear array transducer structure, which generates two intersecting orthogonal imaging planes to provide 3D orientation in the field of view. However, this type of biplane probe is limited to only one imaging plane, since the two imaging planes intersect over one transducer, not along the biopsy needle. A second type of a biplane probe utilizes a convex and flat side-fire linear array transducer structure, which generates two non-intersecting orthogonal imaging planes to provide an indication of 3D orientation. However, this second type of a biplane endocavitary probe does not allow viewing of a biopsy needle in either imaging plane.

Thus, what is desired is an ultrasound endocavitary probe that provides simultaneous viewing of an instrument, such as a biopsy needle or other instrument, in two imaging planes.

SUMMARY OF THE INVENTION

The present invention provides methods and apparatuses for providing simultaneous viewing of an instrument in two ultrasound imaging planes. In one embodiment of the invention, an ultrasound imaging probe is provided which can generate at least two ultrasound imaging planes. In one embodiment, the two imaging planes are not parallel (i.e., the planes intersect). An instrument path is positioned with respect to the planes such that an instrument may be simultaneously viewed in both imaging planes. In one embodiment, the instrument path is provided at an intersection that, at least partially, defines the intersection of the two imaging planes.

DETAILED DESCRIPTION

The present invention provides an ultrasound imaging device that provides simultaneous access to an instrument in at least two imaging planes. In one embodiment of the invention, based on simultaneously imaging the instrument in two imaging planes, three-dimensional (3D) biplane orientation of the instrument and/or other structures may be generated. In one embodiment wherein the invention is embodied in an endocavitary biopsy probe used in medical applications, the instrument may be a biopsy needle that is simultaneously guided through the two imaging planes. It should be appreciated that in this embodiment, the probe may be used to provide images in one plane as well. For example, an endocavitary biopsy probe embodying the invention may be manipulated within the rectum or other cavity for oblique side-fire scanning. However, it should be appreciated that while the invention is primarily described herein with reference to endocavitary biopsy, one or a combination of the ultrasound imaging apparatuses and methods disclosed herein may be utilized in various other medical or non-medical applications without departing from the scope of the invention. Thus, the invention should not necessarily be limited to endocavitary biopsy probes or medical purpose imaging devices.

In the following description, numerous specific details are set forth to provide a thorough understanding of the invention. However, it is understood that the invention may be practiced without these specific details. In other instances, well-known circuits, structures and techniques have not been shown in detail to avoid obscuring the invention.

Figure 1:
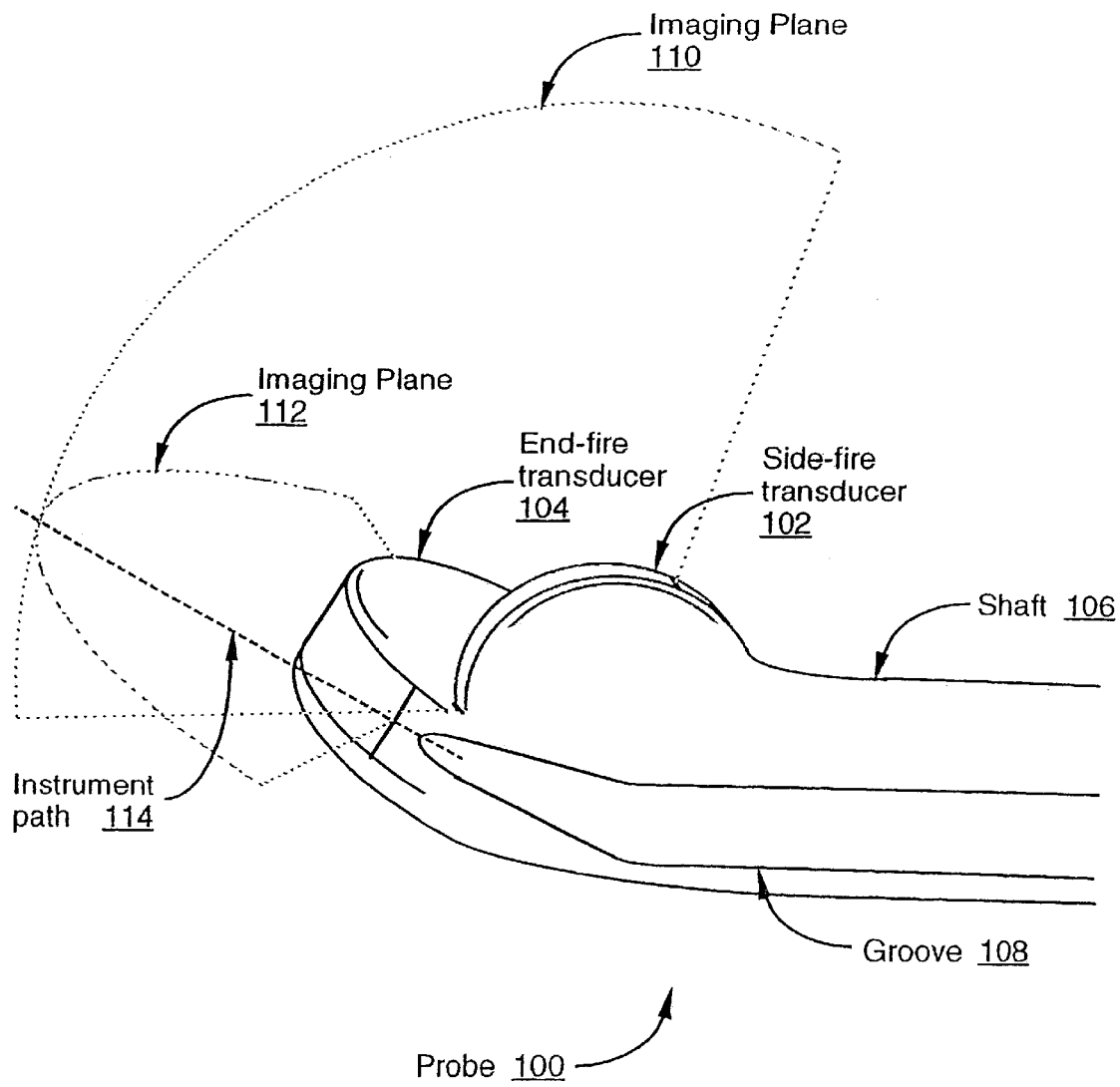
FIG. 1 is a side view diagram of a (portion of) an ultrasound imaging probe for providing simultaneous biplane imaging, according to one embodiment of the invention.

FIG. 1 is a side view diagram of a (portion of) an ultrasound imaging probe for providing simultaneous biplane imaging, according to one embodiment of the invention. In FIG. 1, at least a portion of an ultrasound imaging probe 100 is shown which is defined by a shaft 106. Joined obliquely to the shaft 106 at a distal end of the probe 100 are two convex transducers, a forward-leaning side-fire transducer 102 and an oblique end-fire transducer 104. However, it will be appreciated from the following description that the invention is not limited to a particular type(s) of transducer.

Figure 3A:
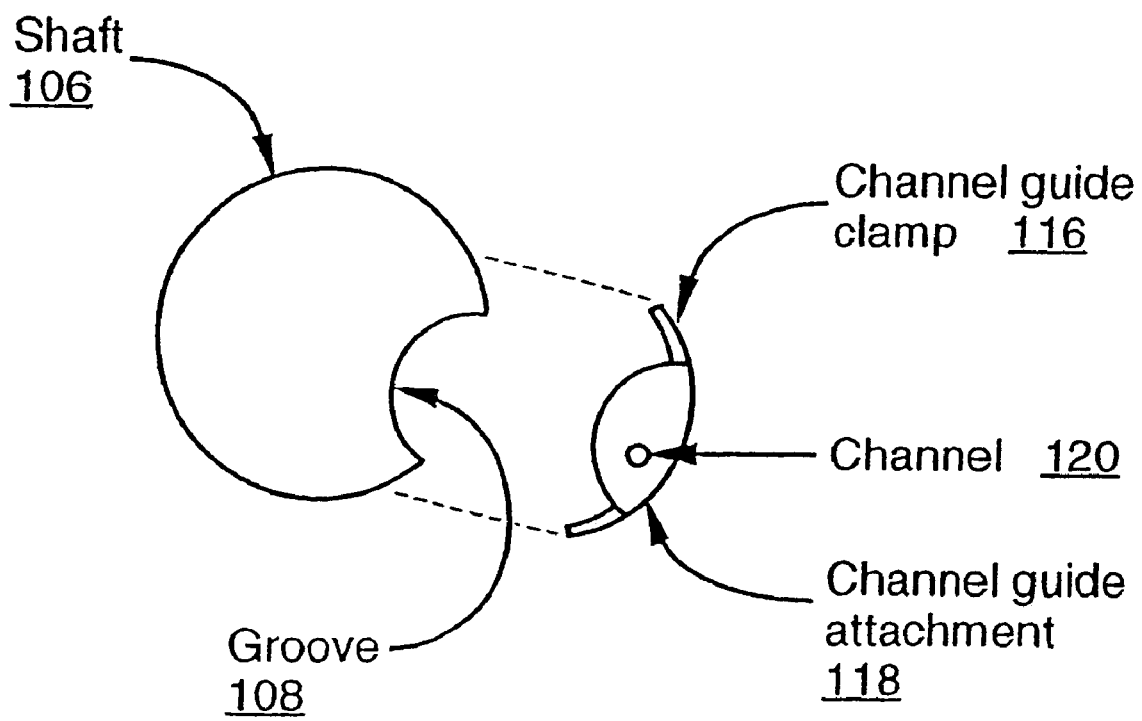
FIG. 3A illustrates a cross-sectional view of an ultrasound probe and channel guide attachment according to the present invention.
Figure 3B:
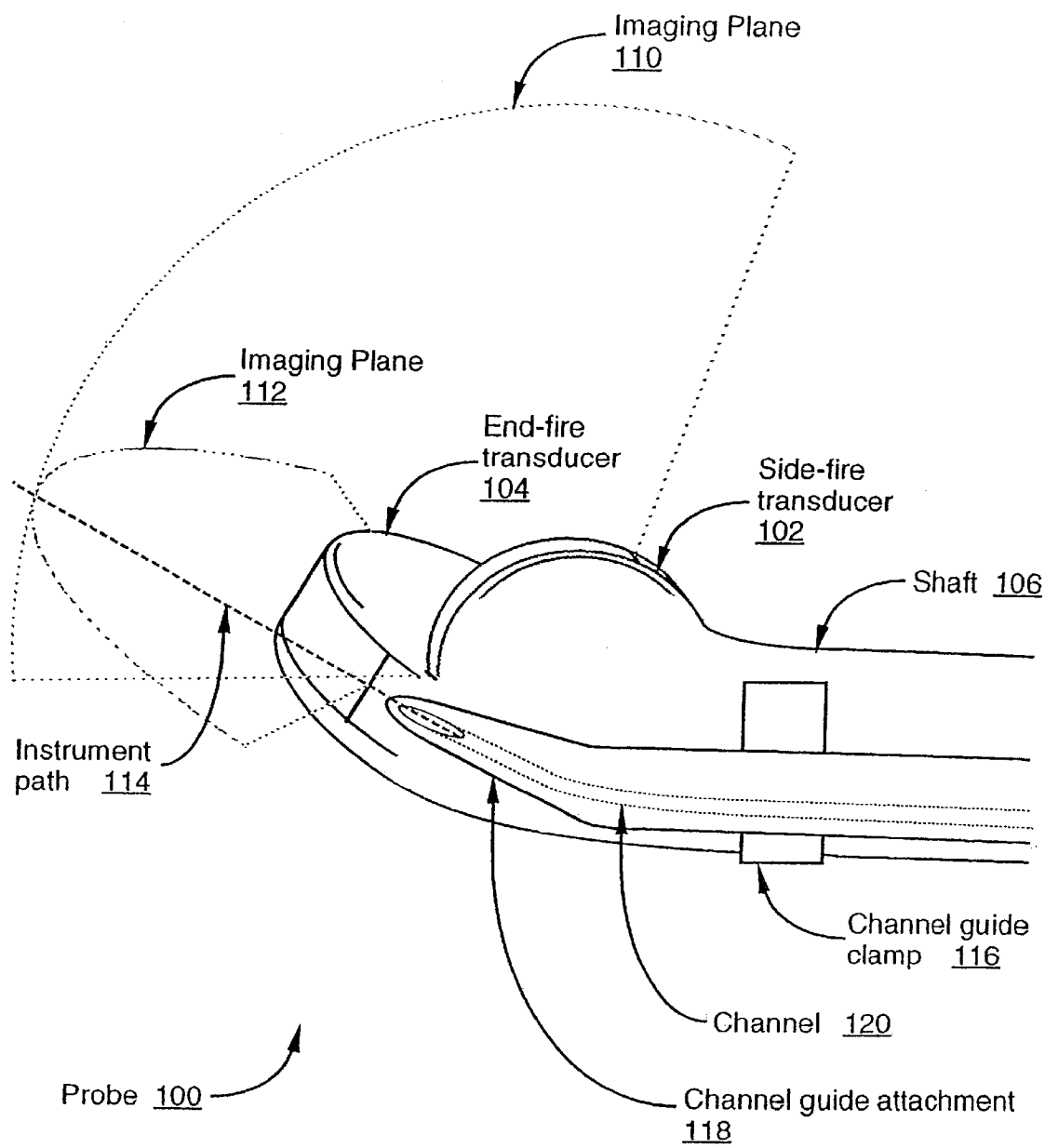
FIG. 3B shows the side view of an ultrasound imaging probe, according to one embodiment of the invention.
Figure 3C:
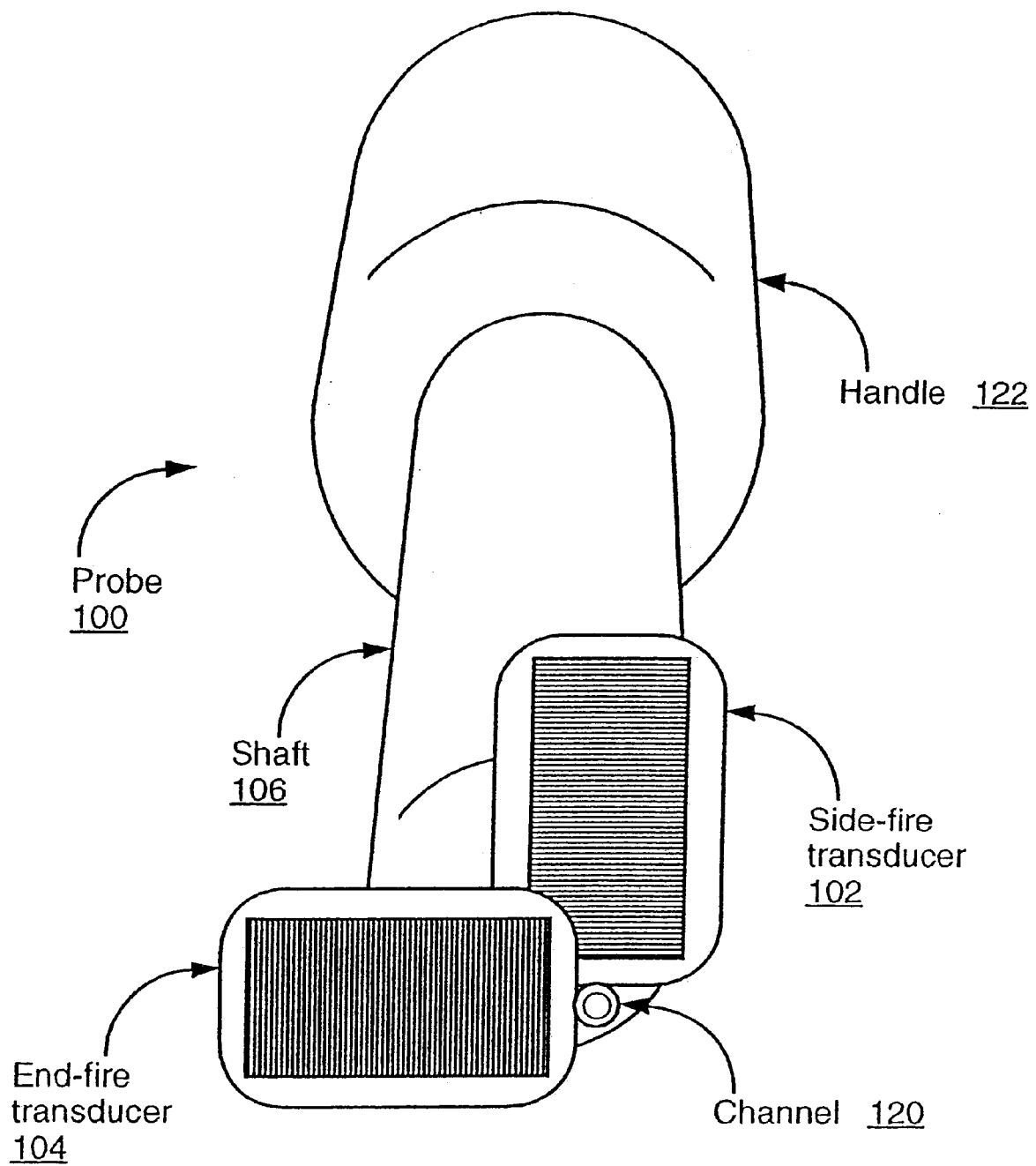
FIG. 3C is an end view of an ultrasound imaging probe, according to one embodiment of the invention.

The side-fire transducer 102 and the end-fire transducer 104 are placed orthogonally relative to each other at the oblique distal end of the probe 100, as shown in FIG. 3C, which depicts a frontal view of one implementation of the probe 100 shown in FIG. 1. As such, the side-fire transducer 102 and the end-fire transducer 104 generate an imaging plane 110 and an imaging plane 112, respectively, which two imaging planes intersect orthogonally, in one embodiment of the invention.

The shaft 106 also defines a groove 108 for providing an instrument path 114. In one embodiment, the groove 108 is configured to accept an attachment having a channel to provide the instrument path 114, such as the channel guide attachment 118 shown in FIGS. 2 and 3A–3C, and described in further detail below. In another embodiment, the groove 108 may be substituted by a channel within the shaft 106 (and the distal end of the probe 100 that includes the transducer assembly) for providing the instrument path 114. The instrument path 114 may be provided, in one embodiment, to a biopsy needle or other instrument for ultrasound image guidance.

In either case, the instrument path 114 substantially lies on a line that defines the intersection of the imaging plane 110 and the imaging plane 112. As such, simultaneous viewing in the imaging plane 110 and the imaging plane 112 of an instrument that is guided in association with the probe 100 along the instrument path 114 may be provided. Thus, a biplane image of the instrument and/or structures in proximity thereto may be generated by processing the image provided by each of the imaging plane 110 and the imaging plane 112. In one embodiment of the invention, a 3D orientation, comprising a composite of two images, each provided by one of the imaging plane 110 and the imaging plane 112, may be provided. In one embodiment, interleaving of images from the two imaging planes may be used to generate the composite of two images. In one embodiment, the probe is coupled to a display system, which includes circuitry and a monitor/display for viewing single or biplane images generated by the probe 100, and in particular, signals derived from the transducers 102 and 104. Such images may be generated according to one or a combination of the above-described ultrasound imaging techniques/devices.

Figure 2:
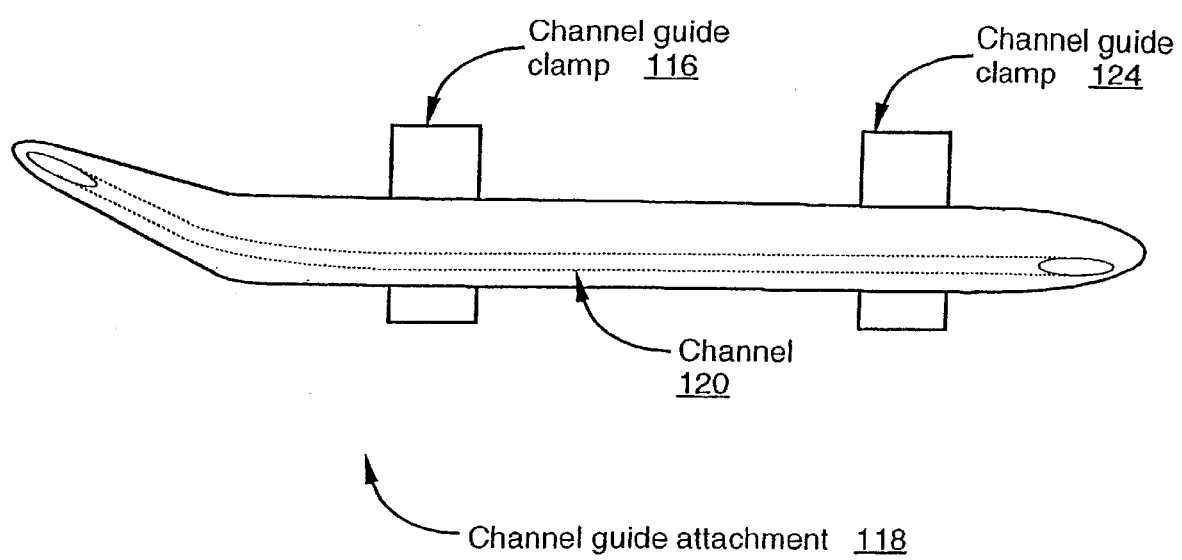
FIG. 2 illustrates a channel guide attachment that may be used with an ultrasound imaging probe, according to one embodiment of the present invention.

FIG. 2 illustrates a channel guide attachment that may be used with an ultrasound imaging probe, according to one embodiment of the present invention. In FIG. 2, a channel guide attachment 118 is shown, which includes a channel guide clamp 116 and a channel guide clamp 124. The channel guide attachment 118 also includes a channel 120 that may be used to facilitate guidance of an instrument (e.g., a biopsy needle). According to one embodiment of the invention, the channel guide attachment 118 may be attached to the probe 100 shown in FIG. 1 and described with reference thereto. In particular, the channel guide attachment 118 may attach to the probe 100 at the groove 108, described above with reference to FIG. 1. In so doing, the channel guide attachment 118 may provide simultaneous access to an instrument, which may be guided through the channel 120, within the imaging plane 112 and the imaging plane 110. The channel guide clamps 116 and 124 shown in FIG. 2 allow the channel guide attachment 118 to be attached to a biopsy imaging probe, such as the probe 100 shown in FIG. 1.

FIG. 3A illustrates a cross-sectional view of an ultrasound probe and channel guide attachment according to the present invention. In particular, FIG. 3A shows the front view of the shaft 106 of the ultrasound imaging probe 100 shown in FIG. 1, along with the channel guide attachment 118, which may be attached thereto. As shown in FIG. 3A, the shaft 106 is defined by the groove 108, as described above with reference to FIG. 1. The channel guide attachment 118 includes the channel 120 as well as the channel guide clamp 116, and may, but not necessarily include other components (e.g., additional channel guide clamps, such as the channel guide clamp 124). In general, FIG. 3A illustrates one configuration for the shaft of an ultrasound probe and compatible channel guide attachment, which may be attached thereto for guidance of an instrument through at least two ultrasound imaging planes. However, it will be appreciated that the channel guide attachment 118, the channel guide clamps 116 and 124, the groove 108, and/or the ultrasound imaging probe 100 may be configured according to several various shapes and sizes to provide simultaneous viewing of an instrument in two or more imaging planes. By providing a detachable/attachable channel guide attachment, in one embodiment of the invention, a probe sheath or cover may be accommodated. In alternative embodiments, the ultrasound imaging probe may not provide a groove and/or other attachment features. For example, a channel for providing an instrument path may be defined by the shaft of the probe itself.

FIG. 3B shows the side view of an ultrasound imaging probe, according to one embodiment of the invention. In particular, FIG. 3B shows the ultrasound imaging probe 100 of FIG. 1 attached to the channel guide attachment 118 attached within the groove 108 (see FIG. 3A). As shown in FIG. 3B and also depicted and described with reference to FIG. 3A, the channel guide attachment 118 may be attached to the probe 100 within the groove 108. In alternative embodiments, the channel guide attachment 118, the channel guide clamps 116 and 124, the groove 108, and/or the ultrasound imaging probe 100 may be configured according to several various shapes and sizes to provide simultaneous viewing of an instrument in two or more imaging planes, such as the imaging planes 110 and 112, via the instrument path 114.

FIG. 3C is an end view of an ultrasound imaging probe, according to one embodiment of the invention. In FIG. 3C, the ultrasound probe 100 is shown in an end view, which shows the offset positioning of the two transducers, namely the side-fire transducer 102 and the end-fire transducer 104, relative to the channel 120. As shown in FIG. 3C, the probe 100 may also include a handle 122.

Figure 4A:
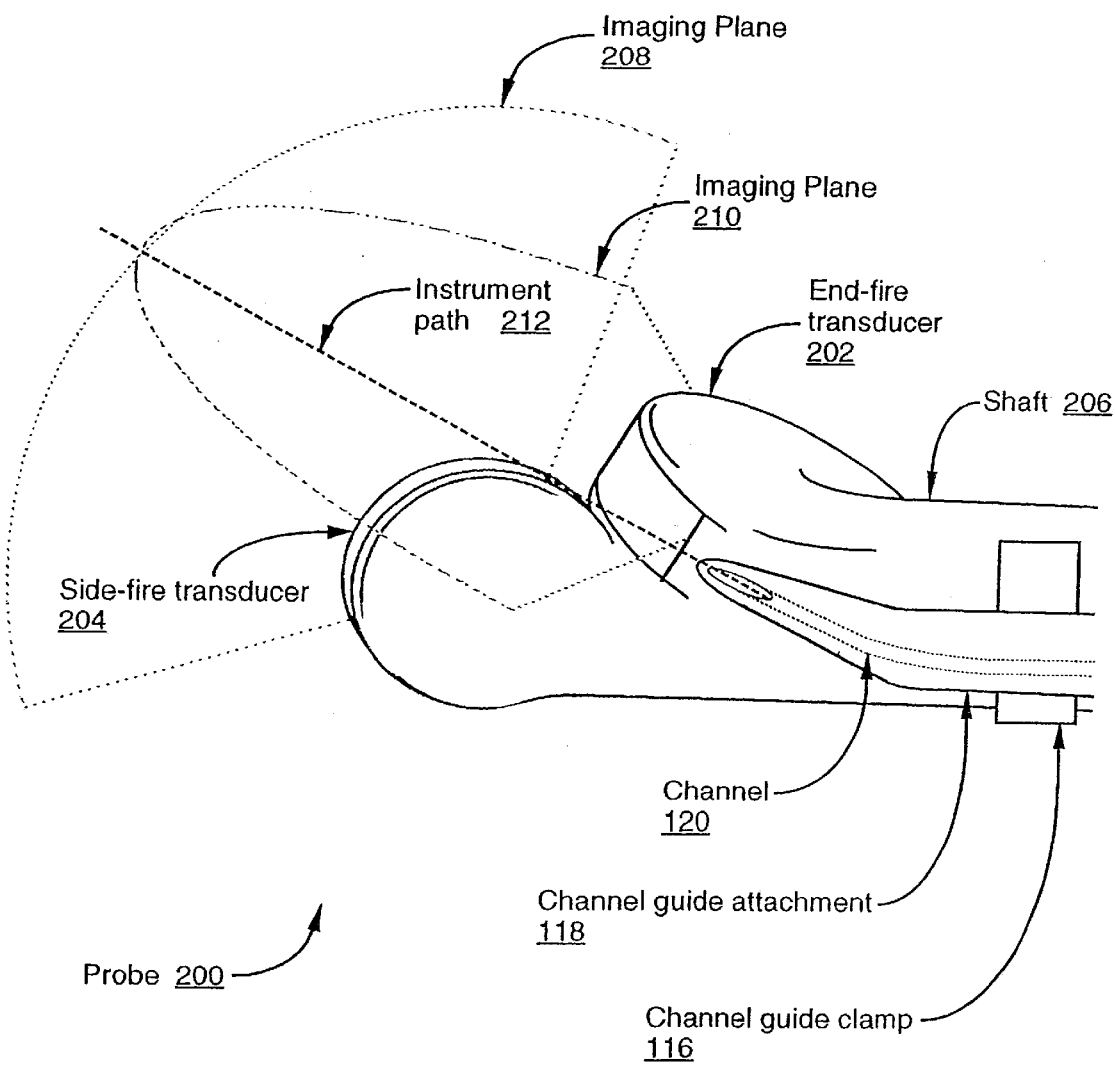
FIG. 4A shows an alternative configuration of an ultrasound imaging probe that provides simultaneous viewing of an instrument in two imaging planes, according to one embodiment of the invention.

FIG. 4A shows an alternative configuration of an ultrasound imaging probe that provides simultaneous viewing of an instrument in two imaging planes, according to one embodiment of the invention. In contrast to the probe 100 described with reference to FIG. 1, the probe 200 shown in FIG. 4A has the positions of the side-fire and end-fire transducers reversed as shown by a side-fire transducer 204 and an end-fire transducer 202, which generate an imaging plane 208 and an imaging plane 210, respectively. Nonetheless, the probe 200 also provides an instrument path, namely the instrument path 212, which provides simultaneous viewing in at least two imaging planes, and in particular, the imaging planes 208 and 210. In one embodiment, the instrument path 212 is defined by the intersection of the imaging plane 208 and the imaging plane 210. As shown in the embodiment of FIG. 4A, the two transducers 202 and 204 are placed orthogonally with respect to each other. As such, the imaging planes 210 and 208, generated by the transducers 202 and 204, respectively, intersect orthogonally. Since the instrument path 212 lies on a line that substantially defines the intersection of the two imaging planes shown in FIG. 4A, the instrument path 212 provides simultaneous viewing of an instrument (e.g. a biopsy needle) in the two imaging planes 208 and 210.

Figure 4B:
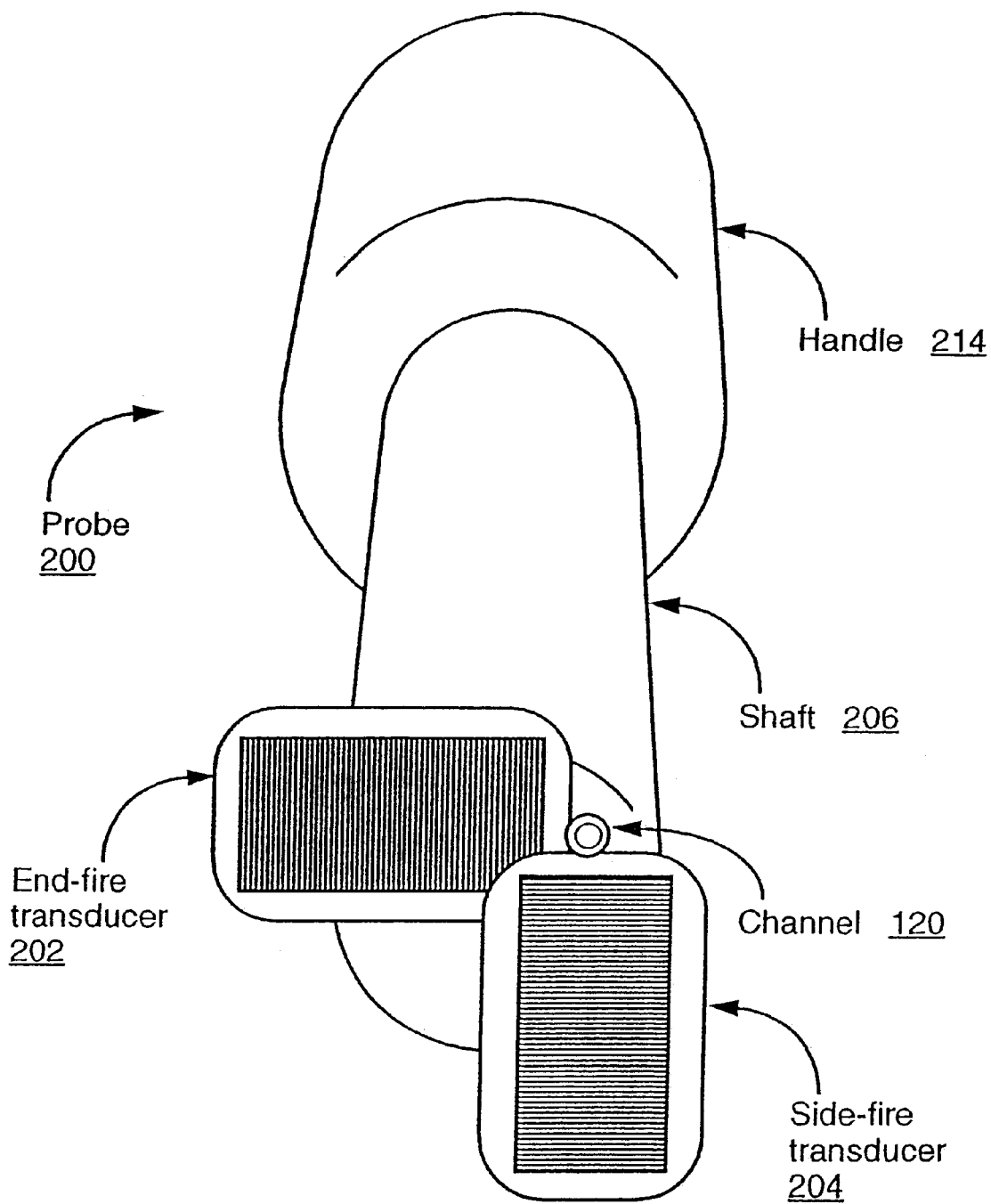
FIG. 4B is an end view an ultrasound imaging probe, according to one embodiment of the invention.

FIG. 4B is an end view an ultrasound imaging probe, according to one embodiment of the invention. In particular, FIG. 4B depicts an end view of the probe 200 shown in FIG. 4A. As shown in FIG. 4B, the probe 200 may include a handle such as the handle 214, and the end view of the probe 200 shows the orientation of the channel 120 relative to the two transducers 202 and 204. As described above with the probe 100, a channel guide attachment, groove, etc., are not necessary to provide an instrument path, such as the channel 108, which provides simultaneous viewing of an instrument in two imaging planes.

Figure 5:
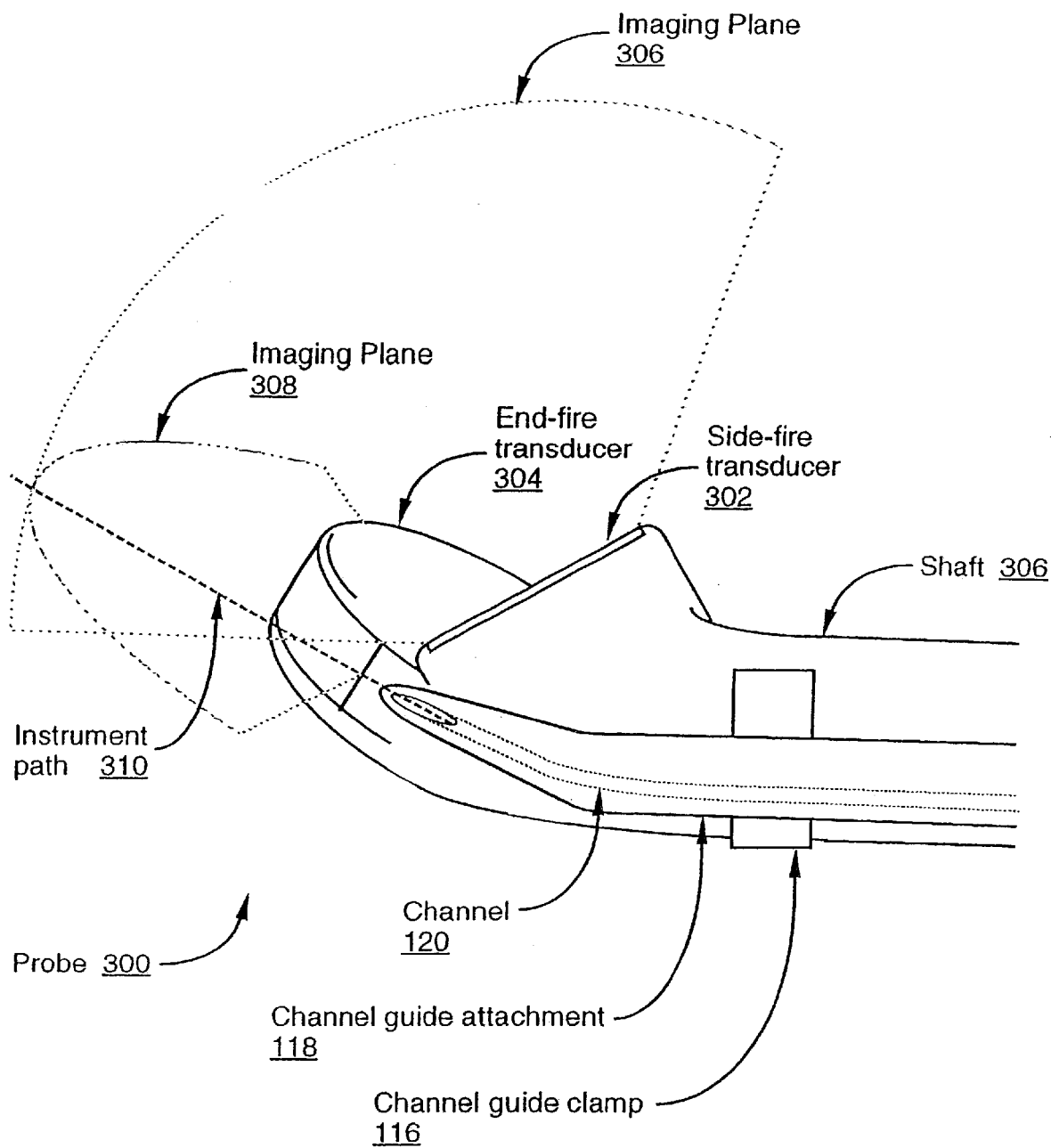
FIG. 5 depicts an ultrasound imaging probe, according to one embodiment of the invention.
Figure 6:
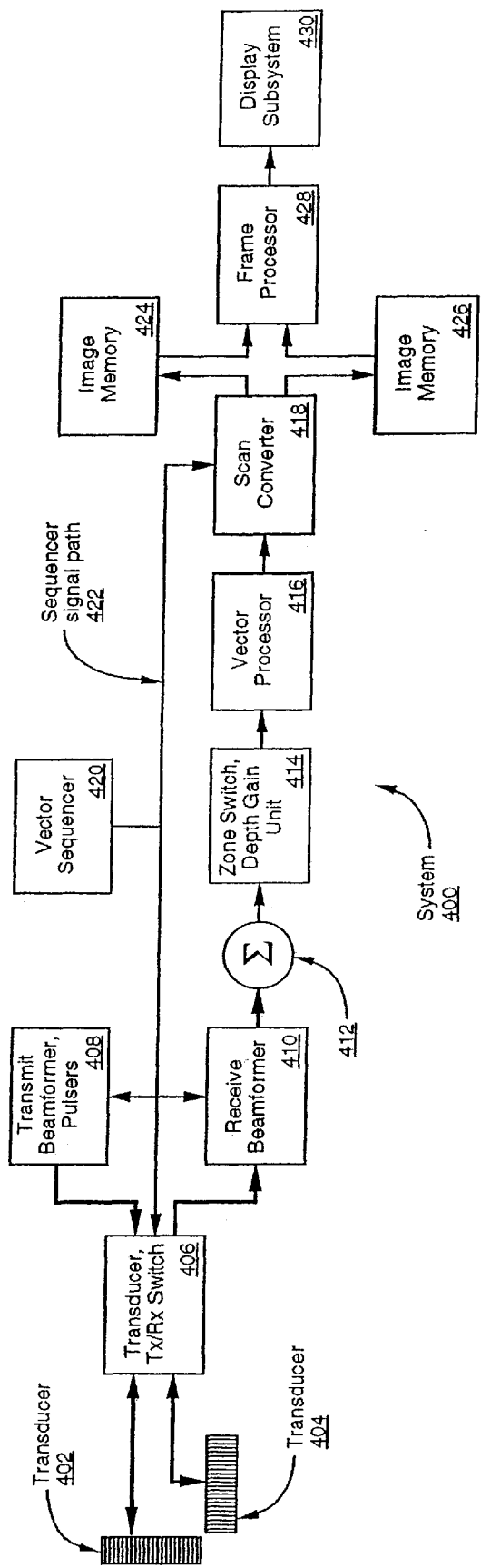
FIG. 6 illustrates an ultrasound imaging system which may provide operation of an ultrasound imaging probe embodying the present invention in simultaneous duplex imaging mode and may be used with a suitable ultrasound scanner, according to one embodiment of the invention.

FIG. 5 depicts an ultrasound imaging probe, according to one embodiment of the invention. In particular, FIG. 5 shows a probe 300 which utilizes a flat phased linear array transducer, according to one embodiment of the invention. The probe 300 includes an oblique end-fire transducer 304 placed orthogonally relative to a flat phased linear array transducer 302. The end-fire transducer 304 and the flat phased linear array transducer 302 generate an imaging plane 308 and an imaging plane 306, respectively, which also intersect orthogonally. An instrument path 310 is shown which provides simultaneous viewing in the imaging planes 306 and 308. According to one aspect of the invention as embodied in the probe 300 shown in FIG. 5, the flat phased linear array transducer 302 may be operated with electronic beam steering to generate a fan image while reducing the cross sectional profile of the probe head. FIG. 6 illustrates an ultrasound imaging system which may provide operation of an ultrasound imaging probe embodying the present invention in simultaneous duplex imaging mode and may be used with a suitable ultrasound scanner, according to one embodiment of the invention. In one embodiment, the system show in FIG. 6 provides real-time frame interleaving of images provided by two transducers to provide dual simultaneous real-time biplane imaging. It will be appreciated that in alternative embodiments of the invention, one or more of the operations of the system depicted in FIG. 6 are not performed in real-time.

As shown in FIG. 6, a system 400 includes a transducer 402 and a transducer 404, both coupled to a transducer transmission/reception (TX/RX) switch 406. The TX/RX switch 406 is coupled to a vector sequencer 420 via a sequencer signal path 422. The vector sequencer 420 is also coupled, via the sequencer signal path 422, to a scan converter 418, whose output is switched between an image memory 424 and an image memory 426, for the respective transducers 402 and 406. The vector sequencer 420, in addition to sequencing vectors within an imaging frame, also sequences vectors between the imaging frames generated by the transducer 402 and the transducer 404, and provided for display to the image memory 424 and the image memory 426, respectively. A transmit beamformer pulser 408 provides signal input to the TX/RX switch 406. In turn, the TX/RX switch 406 is coupled to provide signal input to a receive beamformer 410. Signals received by the receive beamformer 410 are provided to a summing unit 412, which in turn provides summed signals to a zone switch/depth gain unit 414. The zone switch depth gain unit 414 is coupled to a vector processor 416 which in turn is coupled to the scan converter 418. The scan converter 418 provides signals to two image memories, namely an image memory 424 and an image memory 426. The image memories 424 and 426 provide signals to a frame processor 428 and a display subsystem 430.

Although FIG. 6 shows one embodiment of a system in which the present invention may find use, it will be appreciated that the invention may be used with several types configurations and architectures of ultrasound imaging devices and systems, which may include various types of transducers, digital signal processing (DSP) circuits, general purpose processors, storage devices/media, Doppler processing routines/circuitry, etc.

ALTERNATIVE EMBODIMENTS

While the invention has been described in terms of several embodiments, those skilled in the art will recognize that the invention is not limited to the embodiments described. For example, while some types of transducers, ultrasound imaging device circuitry, probe/channel guide attachments, etc., have been shown and described, it will be appreciated that the invention is not limited to such. Accordingly, it will be appreciated that the invention may be embodied in various probe configurations and imaging system architectures that provide simultaneous viewing of an instrument (e.g., an endocavitary biopsy needle) in at least two ultrasound imaging planes.

Therefore, it should be understood that the method and apparatus of the invention can be practiced with modification and alteration within the spirit and scope of the appended claims. The description is thus to be regarded as illustrative instead of limiting on the invention.

What is claimed is:

1. An ultrasound imaging apparatus comprising:
   a first transducer to provide a first imaging plane;
   a second transducer to provide a second imaging plane, wherein said first imaging plane and said second imaging plane intersect orthogonally; and
   a guide to provide simultaneous viewing of a separate instrument in said first and second imaging planes.

2. The ultrasound imaging apparatus of claim 1, wherein:
   said first transducer comprises a side-fire transducer: and
   said second transducer comprises an end-fire transducer.

3. The ultrasound imaging apparatus of claim 2, further comprising a display to provide an image of said instrument, said image being based on simultaneous imaging provided from said first and second imaging planes.

4. The ultrasound imaging apparatus of claim 2, wherein said first and second transducers are positioned orthogonally at the distal end of an endocavitary probe.

5. The ultrasound imaging apparatus of claim 4, wherein said endocavitary probe is defined by a central axis, and wherein said positioning of said first and second transducers is offset from said central axis.

6. The ultrasound imaging apparatus of claim 4, further comprising a guide which defines a channel, said channel to provide said instrument path which substantially passes through a line defining the intersection of said first and second imaging planes.

7. The ultrasound imaging apparatus of claim 6 wherein said guide is detachable to accommodate a probe sheath.

8. The ultrasound imaging apparatus of claim 6, wherein said guide is detachable from said endocavitary probe.

9. The ultrasound imaging apparatus of claim 8, wherein said channel provides access to said instrument.

10. The ultrasound imaging apparatus of claim 8, wherein said probe comprises a shaft, and wherein said distal end of said probe is oblique relative to said shaft.

11. The ultrasound imaging apparatus of claim 10, wherein said shaft defines a groove that provides attachment of said guide.

12. The ultrasound imaging apparatus of claim 11, wherein said guide may be detached from said groove.

13. The ultrasound imaging apparatus of claim 2, wherein an image is generated based on one of three modes, wherein a first mode includes an image based on side-fire, a second mode includes an image based on end-fire, and a third mode includes an image based on a combination of side-fire and end-fire.

14. The ultrasound imaging apparatus of claim 2, wherein at least one of said first and second transducers comprises a convex linear array transducer.

15. The ultrasound imaging apparatus of claim 2, wherein at least one of said first and second transducers comprises a flat phased linear array transducer.

16. The ultrasound imaging apparatus of claim 2, wherein said instrument comprises a biopsy needle.

17. The ultrasound imaging apparatus of claim 2 wherein said end-fire transducer is distal said side-fire transducer.

18. The ultrasound imaging apparatus of claim 2 wherein said side-fire transducer is a forward leaning side-fire transducer and said end-fire transducer is an oblique end-fire transducer.

19. An apparatus for performing endocavitary ultrasound imaging, said apparatus comprising:
    a first means for generating a first imaging plane;
    a second means for generating a second imaging plane, wherein said first imaging plane and said second imaging plane intersect orthogonally; and
    a third means for providing simultaneous viewing of a separate instrument in said first and second imaging planes.

20. The apparatus of claim 19, further comprising a display means for displaying an image representing said simultaneous viewing of said instrument in said first and second imaging planes.

21. The apparatus of claim 19, wherein said third means comprises a path means for providing a path for said instrument, said path being defined by an intersection of said first and second imaging planes.

22. A method for performing endocavitary ultrasound imaging, said method comprising:
    generating an image of an instrument applicable via an endocavitary probe, said image based on views of said instrument simultaneously generated in at least two imaging planes, wherein said two imaging planes intersect orthogonally, said instrument separate from said endocavitary probe; and
    displaying said image.

23. A method for performing endocavitary ultrasound biopsy, said method comprising:
    generating a first image associated with a first imaging plane;
    generating a second image associated with a second imaging plane, said second image plane intersecting said first image plane orthogonally;
    providing a guide to allow simultaneous imaging of an instrument separate from said guide in said first and second imaging planes;
    generating a composite image of an instrument, said composite image being based on said first and second images from said first and second imaging planes, respectively.

24. The method of claim 23, wherein:
    said first image is generated by a first transducer, which comprises a side-fire transducer: and
    said second image is generated by a second transducer, which comprises an end-fire transducer.

25. The method of claim 24, wherein said first and second transducers are positioned orthogonally at the distal end of an endocavitary probe.

26. The method of claim 25, wherein said endocavitary probe is defined by a central axis, and wherein said first and second transducers are at a location offset from said central axis.

27. The method of claim 24, further comprising generating an image based on one of three modes, wherein a first mode includes an image based on side-fire, a second mode includes an image based on end-fire, and a third mode includes an image based on a combination of side-fire and end-fire.

28. The ultrasound imaging apparatus of claim 24, wherein at least one of said first and second transducers comprises a convex linear array transducer.

29. The ultrasound imaging apparatus of claim 24, wherein at least one of said first and second transducers comprises a flat phased linear array transducer.

30. The method of claim 23, further comprising:

inserting said instrument, via said guide, to generate said composite image.

31. The method claim 30, further comprising displaying said composite image of said instrument.

32. The method of claim 23, further comprising:

providing a channel substantially passing through a line defining the intersection of said first and second imaging planes.

33. The method of claim 32, wherein said channel is provided by a guide, and wherein said guide is attached to a shaft of an endocavitary probe.

34. The method of claim 33, wherein said instrument comprises a biopsy needle.

35. The method of claim 33, wherein said probe is defined by a distal end, which is oblique relative to said shaft of said probe.

36. The method of claim 35, wherein said shaft defines a groove that provides attachment of said guide.

* * * * *